US012596131B2

(12) United States Patent
Lanpheer

(10) Patent No.: US 12,596,131 B2
(45) Date of Patent: Apr. 7, 2026

(54) SYSTEM AND METHODS FOR LAB AUTOMATION DATA SHARING

(71) Applicant: Gen-Probe Incorporated, San Diego, CA (US)

(72) Inventor: John Lanpheer, San Diego, CA (US)

(73) Assignees: Gen-Probe Incorporated, San Diego, CA (US); Grifols, S.A., Barcelona (ES)

( * ) Notice: Subject to any disclaimer, the term of this patent is extended or adjusted under 35 U.S.C. 154(b) by 953 days.

(21) Appl. No.: 17/781,249

(22) PCT Filed: Dec. 1, 2020

(86) PCT No.: PCT/US2020/062703
§ 371 (c)(1),
(2) Date: May 31, 2022

(87) PCT Pub. No.: WO2021/113238
PCT Pub. Date: Jun. 10, 2021

(65) Prior Publication Data
US 2022/0412999 A1 Dec. 29, 2022

Related U.S. Application Data

(60) Provisional application No. 62/947,979, filed on Dec. 13, 2019, provisional application No. 62/942,539, filed on Dec. 2, 2019.

(51) Int. Cl.
*G01N 35/00* (2006.01)
*G16H 10/40* (2018.01)

(52) U.S. Cl.
CPC . *G01N 35/00871* (2013.01); *G01N 35/00623* (2013.01); *G16H 10/40* (2018.01); *G01N 2035/00881* (2013.01)

(58) Field of Classification Search
CPC ............. G16H 10/40; G01N 35/00663; G01N 35/00623; G01N 35/00871; G01N 35/00722; G01N 2035/00881
See application file for complete search history.

(56) References Cited

U.S. PATENT DOCUMENTS

| | | | |
|---|---|---|---|
| 5,357,095 A | 10/1994 | Weyrauch et al. | |
| 6,581,012 B1 | 6/2003 | Aryev et al. | |
| (Continued) | | | |

FOREIGN PATENT DOCUMENTS

| | | |
|---|---|---|
| CN | 101910838 A | 12/2010 |
| CN | 103392181 A | 11/2013 |
| (Continued) | | |

OTHER PUBLICATIONS

Beckman Coulter Inc., Automated Chemistry Analyzer, AU2700 ® User's Guide, 2000, vol. 1, pp. 1-377, Beckman Coulter Inc., USA.
(Continued)

*Primary Examiner* — Shogo Sasaki
(74) *Attorney, Agent, or Firm* — Rothwell, Figg, Ernst & Manbeck, P.C.; Charles B. Cappellari

(57) ABSTRACT

A method for sharing system information data in a network of two or more diagnostic instruments for performing assays is provided. The system information data includes operating information for the diagnostic instruments in the network. The method includes: sending a system information metadata packet to at least a first diagnostic instrument in the network, wherein the system information metadata packet, is associated with system information data on a second diagnostic instrument in the network and comprises one or more attributes of a system information data packet containing the associated system information data; receiving a request from the first diagnostic instrument to send the system information data packet, and in response to the request from the first diagnostic instrument to send the system information data
(Continued)

packet, sending the system information data packet containing the associated system information data to the first diagnostic instrument.

7 Claims, 7 Drawing Sheets

(56) References Cited

U.S. PATENT DOCUMENTS

| | | | |
|---|---|---|---|
| 7,556,771 B2 | 7/2009 | Nakamura et al. | |
| 7,732,212 B1 | 6/2010 | Nakata et al. | |
| 7,860,727 B2* | 12/2010 | Showalter | G06Q 10/00 |
| | | | 705/2 |
| 7,883,015 B2 | 2/2011 | Ackermann et al. | |
| 8,065,764 B2 | 11/2011 | Kramer | |
| 8,318,499 B2 | 11/2012 | Fritchie et al. | |
| 8,719,053 B2 | 5/2014 | Showalter et al. | |
| 8,728,007 B2 | 5/2014 | Azer et al. | |
| 9,127,313 B2 | 9/2015 | Brown et al. | |
| 9,201,083 B2 | 12/2015 | Wakamiya | |
| 9,377,452 B2 | 6/2016 | Bartel et al. | |
| 9,477,814 B2 | 10/2016 | Wan et al. | |
| 9,835,640 B2 | 12/2017 | Raicu et al. | |
| 9,852,016 B2 | 12/2017 | Griffith et al. | |
| 9,880,528 B2 | 1/2018 | Mastrototaro et al. | |
| 9,927,941 B2 | 3/2018 | Steimle et al. | |
| 9,953,141 B2* | 4/2018 | Scott | G16H 10/40 |
| 10,024,734 B2 | 7/2018 | Tirinato et al. | |
| 10,181,010 B2 | 1/2019 | Patel et al. | |
| 10,557,862 B2 | 2/2020 | Glavina et al. | |
| 10,867,274 B2 | 12/2020 | Jones et al. | |
| 10,970,301 B2* | 4/2021 | Schiefner | G06F 16/2456 |
| 11,032,324 B2* | 6/2021 | Buckley | H04W 12/062 |
| 11,355,220 B2 | 6/2022 | Scott et al. | |
| 11,474,533 B2 | 10/2022 | Forsberg et al. | |
| 11,562,514 B2* | 1/2023 | Tarnawski | G16H 40/20 |
| 12,155,663 B2* | 11/2024 | Yada | H04L 63/102 |
| 2002/0082957 A1 | 6/2002 | Krassi | |
| 2005/0159982 A1 | 7/2005 | Showalter et al. | |
| 2005/0186114 A1 | 8/2005 | Reinhardt et al. | |
| 2006/0148063 A1 | 7/2006 | Fauzzi et al. | |
| 2006/0178776 A1 | 8/2006 | Feingold et al. | |
| 2007/0176790 A1 | 8/2007 | Klabunde et al. | |
| 2008/0024301 A1 | 1/2008 | Fritchie et al. | |
| 2008/0235055 A1 | 9/2008 | Mattingly et al. | |
| 2009/0089004 A1 | 4/2009 | Vook et al. | |
| 2009/0151479 A1 | 6/2009 | Bartel et al. | |
| 2009/0204660 A1 | 8/2009 | Chappell | |
| 2010/0001854 A1 | 1/2010 | Kojima et al. | |
| 2011/0238704 A1 | 9/2011 | Koike et al. | |
| 2011/0246215 A1 | 10/2011 | Postma et al. | |
| 2011/0296011 A1* | 12/2011 | Dare | G06F 9/544 |
| | | | 709/224 |
| 2012/0110173 A1* | 5/2012 | Luna | H04L 67/145 |
| | | | 709/224 |
| 2012/0275956 A1 | 11/2012 | Wakamiya et al. | |
| 2012/0324091 A9* | 12/2012 | Raleigh | H04L 41/0894 |
| | | | 709/224 |
| 2013/0055373 A1* | 2/2013 | Beacham | H04L 47/29 |
| | | | 726/13 |
| 2013/0124607 A1* | 5/2013 | Griffith | H04L 43/50 |
| | | | 709/203 |
| 2013/0124718 A1* | 5/2013 | Griffith | H04L 43/103 |
| | | | 709/224 |
| 2013/0124752 A1* | 5/2013 | Griffith | G06F 11/3093 |
| | | | 709/235 |
| 2013/0145299 A1 | 6/2013 | Steimle et al. | |
| 2013/0274139 A1 | 10/2013 | Burd et al. | |
| 2013/0326109 A1 | 12/2013 | Kivity | |
| 2013/0346109 A1 | 12/2013 | Gunn | |
| 2014/0252088 A1 | 9/2014 | Cong et al. | |
| 2015/0104796 A1 | 4/2015 | Goemann-Thoss et al. | |
| 2015/0314246 A1 | 11/2015 | Lehtonen et al. | |
| 2016/0161516 A1 | 6/2016 | Fritchie et al. | |
| 2016/0356801 A1 | 12/2016 | Glavina et al. | |
| 2017/0082585 A1 | 3/2017 | DeWitte et al. | |
| 2017/0231508 A1 | 8/2017 | Edwards et al. | |
| 2018/0032954 A1 | 2/2018 | Barnes et al. | |
| 2018/0225139 A1 | 8/2018 | Hahn et al. | |
| 2018/0226139 A1 | 8/2018 | Scott et al. | |
| 2019/0072575 A1 | 3/2019 | Oosterbroek et al. | |
| 2019/0107548 A1 | 4/2019 | Bohnsack et al. | |
| 2023/0334423 A1* | 10/2023 | Barnes | G16B 99/00 |

FOREIGN PATENT DOCUMENTS

| | | |
|---|---|---|
| JP | H08329160 A | 12/1996 |
| JP | 2003315345 A | 11/2003 |
| JP | 3127156 U | 11/2006 |
| JP | 2007518479 A | 7/2007 |
| JP | 2008224384 A | 9/2008 |
| JP | 4939231 B2 | 5/2012 |
| JP | 2014062760 A | 4/2014 |
| JP | 2015114122 A | 6/2015 |
| WO | 2005/066872 A2 | 7/2005 |
| WO | 2006/081103 A1 | 8/2006 |
| WO | 2016040985 A1 | 3/2016 |
| WO | 2016071993 A1 | 5/2016 |
| WO | 2016/195896 A1 | 12/2016 |
| WO | 2018/210721 A1 | 11/2018 |

OTHER PUBLICATIONS

Abbott, i-STAT ® 1 System Manual, Abbott Point of Care, 2017, pp. 1-606, Abbott of Point Care Inc., USA.

Novartis Vaccines and Diagnostics, Inc., Procleix ® TIGRIS System, Operator's Manual, vol. I: Operating the Instrument, 2010, pp. 1-155, Gen-Probe and Novartis Diagnositcs, USA.

Breese et al., "Labrat LIMS: An Extensible Framework for Developing Laboratory Information Management, Analysis, and Bioinformatics Solutions for Microarrays," ACM, 2003, pp. 103-108, SAC Melbourne FL., USA.

Krunićet al., "Software for automatic control of laboratory analysis," 21st Telecommunications forum TELFOR, 2013, pp. 1023-1026, Serbia, Belgrade.

Sparkes et al., "AutoLabDB: a substantial open source database schema to support a high-throughput automated laboratory," BioInformatics, 2012, vol. 28(10):1390-1397, Oxford University Press, UK.

CIPO Examiner's Report, Canadian Application No. 3,163,473, Apr. 29, 2025.

International Preliminary Report on Patentability dated May 17, 2022 in International Application No. PCT/US2020/062703 (13 pages).

European Examination Report dated Apr. 18, 2024 in European Application No. 20 828 718.5 (12 pages).

Canadian First Examiner Report dated Apr. 4, 2024 in Canadian Application No. 3,163,473 (5 pages).

International Search Report and Written Opinion dated Mar. 17, 2021 in International Application No. PCT/US2020/062703 (15 pages).

APO Examiner's Report No. 1, Australian Application No. 2020398164, Nov. 10, 2025.

* cited by examiner

Apparatus
600

MODULE(S)
700

FIG. 7

SYSTEM AND METHODS FOR LAB AUTOMATION DATA SHARING

CROSS REFERENCE TO RELATED APPLICATION(S)

This application is a 35 U.S.C. § 371 National Stage of International Patent Application No. PCT/US2020/062703, filed Dec. 1, 2020, and claims priority to provisional applications U.S. Ser. No. 62/942,539, filed Dec. 2, 2019, and U.S. Ser. No. 62/947,979, filed Dec. 13, 2019, both of which are titled "System and Methods for Lab Automation Data Sharing," the respective disclosures of which are hereby incorporated by reference in their entirety.

FIELD OF THE DISCLOSURE

This disclosure relates to automated systems and methods for data sharing in a laboratory environment among two or more analyzers for performing diagnostic assays.

BACKGROUND

Laboratories sometimes use multiple analyzers for performing molecular assays. As part of the molecular assay process, reagents are used. Such reagents may be volatile, may require certain storage conditions, may have short shelf-lives, and may have a limited number of uses. For example, reagents are typically kept in an analyzer only during the day when the analyzer is being used, and are stored at night elsewhere (e.g., in refrigerator units) in order to better maintain the reagent so that it may be used longer. It is important that information regarding the reagent (such as amount of reagent previously used, expiration date, and so on) is accurately updated and stored so that assays can be successfully completed. For example, if an assay were performed with an expired reagent, or with a reagent for which there were not a sufficient amount remaining, the results of the assay (if it were even able to be completed) would not be reliable.

Current practice is to manually log which analyzer a given reagent has been used on, and when removing the reagent from storage to again insert the reagent into the same analyzer it has previously been used on. The analyzer may then recognize the reagent, and access its own internal store of information regarding the reagent. In this way, the analyzer can be certain that the reagent is (or is not) fit for continued use. If the reagent were instead inserted into a new analyzer, which had not seen the reagent before, the analyzer would have no way to determine information about the reagent that is subject to change with use. For example, the new analyzer would not know what quantity of the reagent (if any) had previously been used, and therefore could not determine how much of the reagent remained for use. As another example, the new analyzer would not know the time that the reagent has been out of cold storage, and therefore could not determine the onboard stability of the reagent. The process of logging which analyzer a given reagent must be used in, and returning that reagent to the specific analyzer each day, is time consuming and also prone to human error. Additionally, the process limits a laboratory operator's ability to freely determine how to allocate reagents among analyzers, and therefore hinders the full and efficient usage of both reagents and analyzers.

SUMMARY

The following presents a simplified summary in order to provide a basic understanding of some aspects described herein. This summary is not an extensive overview of the claimed subject matter. It is intended to neither identify key or critical elements of the claimed subject matter nor delineate the scope thereof. Its sole purpose is to present some concepts in a simplified form as a prelude to the more detailed description that is presented later.

Accordingly, there is a need in the art for an improved analyzer system. In particular, there is a need for sharing information between analyzers for performing molecular assays, such that different analyzers in a system may be made aware of changing information, allowing reagents to be freely used among any of the analyzers in the system. Sharing information among analyzers may also result in other benefits, such as simplified and streamlined administration, and support for additional testing integrity.

According to a first aspect, a method for sharing system information data in a network of two or more diagnostic instruments for performing assays is provided. The system information data may include operating information for the diagnostic instruments in the network. The method may include sending a system information metadata packet to at least a first diagnostic instrument in the network. The system information metadata packet may be associated with system information data on a second diagnostic instrument in the network and may include one or more attributes of a system information data packet containing the associated system information data. The method may further include receiving a request from the first diagnostic instrument to send the system information data packet. The method may further include, in response to the request from the first diagnostic instrument to send the system information data packet, sending the system information data packet containing the associated system information data to the first diagnostic instrument.

According to a second aspect, a method for sharing system information data in a network of two or more diagnostic instruments for performing assays is provided. The system information data may comprise operating information for the diagnostic instruments in the network. The method may include receiving a system information metadata packet by a first diagnostic instrument in the network. The system information metadata packet may be associated with system information data on a second diagnostic instrument in the network and may include one or more attributes of a system information data packet containing the associated system information data. The method may further include determining from the system information metadata packet that the first diagnostic instrument needs the associated system information data contained in the system information data packet. The method may further include, in response to determining from the system information metadata packet that the first diagnostic instrument needs the associated system information data contained in the system information data packet, sending a request to the second diagnostic instrument to send the system information data packet. The method may further include receiving the system information data packet containing the associated system information data from the second diagnostic instrument.

In some embodiments, the system information data further comprises information about one or more of: users, master lots for assay reagents, controls, calibrators, assay reagent kits, assay cartridges, and external quality control (EQC) definitions.

According to a third aspect, a method for sharing data in a diagnostic environment is provide. The method may include receiving, by a first diagnostic instrument for performing assays, information from a second diagnostic instrument for performing assays, where the information may include attributes of an assay reagent. The information may include an expiration date for the assay reagent. The method may further include receiving the assay reagent for performing an assay. The method may further include correlating the information with the received assay reagent. The method may further include, prior to performing an assay with the assay reagent, analyzing the information to determine whether the assay reagent is viable.

In some embodiments, the method may further include performing the assay with the assay reagent. In some embodiments, receiving, by a first diagnostic instrument for performing assays, information from a second diagnostic instrument for performing assays may include: receiving, by the first diagnostic instrument, metadata from the second diagnostic instrument, the metadata describing a data change event; determining, by the first diagnostic instrument, that the data change event needs to be applied to the first diagnostic instrument; sending a request, by the first diagnostic instrument, in response: to the determining, to the second diagnostic instrument, the request being for the data associated with the data change event; and receiving, by the first diagnostic instrument, the data associated with the data change event from the second diagnostic instrument. In some embodiments, the information further comprises information about one or more of: users, master lots for assay reagents, controls, calibrators, assay reagent kits, assay cartridges, and external quality control (EQC) definitions.

According to a fourth aspect, a method for sharing data in a diagnostic environment is provided. The method may include receiving, by a first diagnostic instrument for performing assays, a reagent kit for performing an assay. The method may further include generating, by the first diagnostic instrument, information describing the reagent kit. The information may include an expiration date for the reagent kit. The method may further include sending, to a second diagnostic instrument for performing assays, the information from the first diagnostic instrument.

In some embodiments, sending, to a second diagnostic instrument for performing assays, the information from the first diagnostic instrument may comprise: sending, by the first diagnostic instrument, metadata to the second diagnostic instrument, the metadata describing a data change event; receiving, at the first diagnostic instrument, a request from the second diagnostic instrument, the request being for the data associated with the data change event; and sending, by the first diagnostic instrument, the data associated with the data change event to the second diagnostic instrument.

According to a fifth aspect, a method for sharing system information data in a network of two or more diagnostic instruments for performing assays is provided. The system information data may comprise operating information for the diagnostic instruments in the network. The method may include transmitting a system information metadata packet from one diagnostic instrument in the network to at least one other diagnostic instrument in the network. The system information metadata packet may be associated with and comprise one or more attributes of a system information data packet. The method may further include determining from the system information metadata packet whether the at least one other diagnostic instrument has the associated system information data packet. The method may further include, if the at least one other diagnostic instrument does not have the associated system information data packet, transmitting the associated system information data packet to the at least one other diagnostic instrument.

In some embodiments, the system information data packet comprises information about one or more of: users, master lots for assay reagents, controls, calibrators, assay reagent kits, assay cartridges, and external quality control (EQC) definitions.

According to a sixth aspect, an analyzer for performing assays is provided. The analyzer may include a processor and instructions which, when executed, may cause the processor to send a system information metadata packet to at least a first diagnostic instrument in the network. The system information metadata packet may e associated with system information data on a second diagnostic instrument in the network and may comprise one or more attributes of a system information data packet containing the associated system information data. The instructions, when executed, may further cause the processor to receive a request from the first diagnostic instrument to send the system information data packet. The instructions, when executed, may further cause the processor to, in response to the request from the first diagnostic instrument to send the system information data packet, send the system information data packet containing the associated system information data to the first diagnostic instrument.

According to a seventh aspect, an analyzer for performing assays is provided. The analyzer may include a processor and instructions which, when executed, may cause the processor to receive a system information metadata packet by a first diagnostic instrument in the network. The system information metadata packet may be associated with system information data on a second diagnostic instrument in the network and may comprise one or more attributes of a system information data packet containing the associated system information data. The instructions, when executed, may further cause the processor to determine from the system information metadata packet that the first diagnostic instrument needs the associated system information data contained in the system information data packet. The instructions, when executed, may further cause the processor to, in response to determining from the system information metadata packet that the first diagnostic instrument needs the associated system information data contained in the system information data packet, send a request to the second diagnostic instrument to send the system information data packet. The instructions, when executed, may further cause the processor to receive the system information data packet containing the associated system information data from the second diagnostic instrument.

According to an eighth aspect, an analyzer for performing assays is provided. The analyzer may include a processor and instructions which, when executed, may cause the processor to receive, by a first diagnostic instrument for performing assays, information from a second diagnostic instrument for performing assays, the information including attributes of an assay reagent. The information may include an expiration date for the assay reagent. The instructions, when executed, may further cause the processor to receive the assay reagent for performing an assay. The instructions, when executed, may further cause the processor to correlate the information with the received assay reagent. The instructions, when executed, may further cause the processor to, prior to performing an assay with the assay reagent, analyze the information to determine whether the assay reagent is viable.

According to a ninth aspect, an analyzer for performing assays is provided. The analyzer may include a processor and instructions which, when executed, may cause the processor to receive, by a first diagnostic instrument for performing assays, a reagent kit for performing an assay. The instructions, when executed, may further cause the processor to generate, by the first diagnostic instrument, information describing the reagent kit. The information may include an expiration date for the reagent kit. The instructions, when executed, may further cause the processor to send, to a second diagnostic instrument for performing assays, the information from the first diagnostic instrument.

According to a tenth aspect, a system including a first analyzer for performing assays and a second analyzer for performing assays is provided. The system may be configured to transmit a system information metadata packet from one diagnostic instrument in the network to at least one other diagnostic instrument in the network. The system information metadata packet may be associated with and may comprise one or more attributes of a system information data packet. The system may be further configured to determine from the system information metadata packet whether the at least one other diagnostic instrument has the associated system information data packet. The system may be further configured to, if the at least one other diagnostic instrument does not have the associated system information data packet, transmit the associated system information data packet to the at least one other diagnostic instrument.

According to an eleventh aspect, a computer program comprising instructions which when executed by processing circuitry causes the processing circuitry to perform the method of any one of the embodiments of the first aspect, the second aspect, the third aspect, the fourth aspect, and the fifth aspect.

According to a twelfth aspect, a carrier containing the computer program of the eleventh aspect is provided. The carrier may be one of an electronic signal, an optical signal, a radio signal, and a computer readable storage medium.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various embodiments of the subject matter of this disclosure. In the drawings, like reference numbers indicate identical or functionally similar elements.

FIG. 7 is a block diagram of an apparatus according to an embodiment.

DETAILED DESCRIPTION

Figure 1:
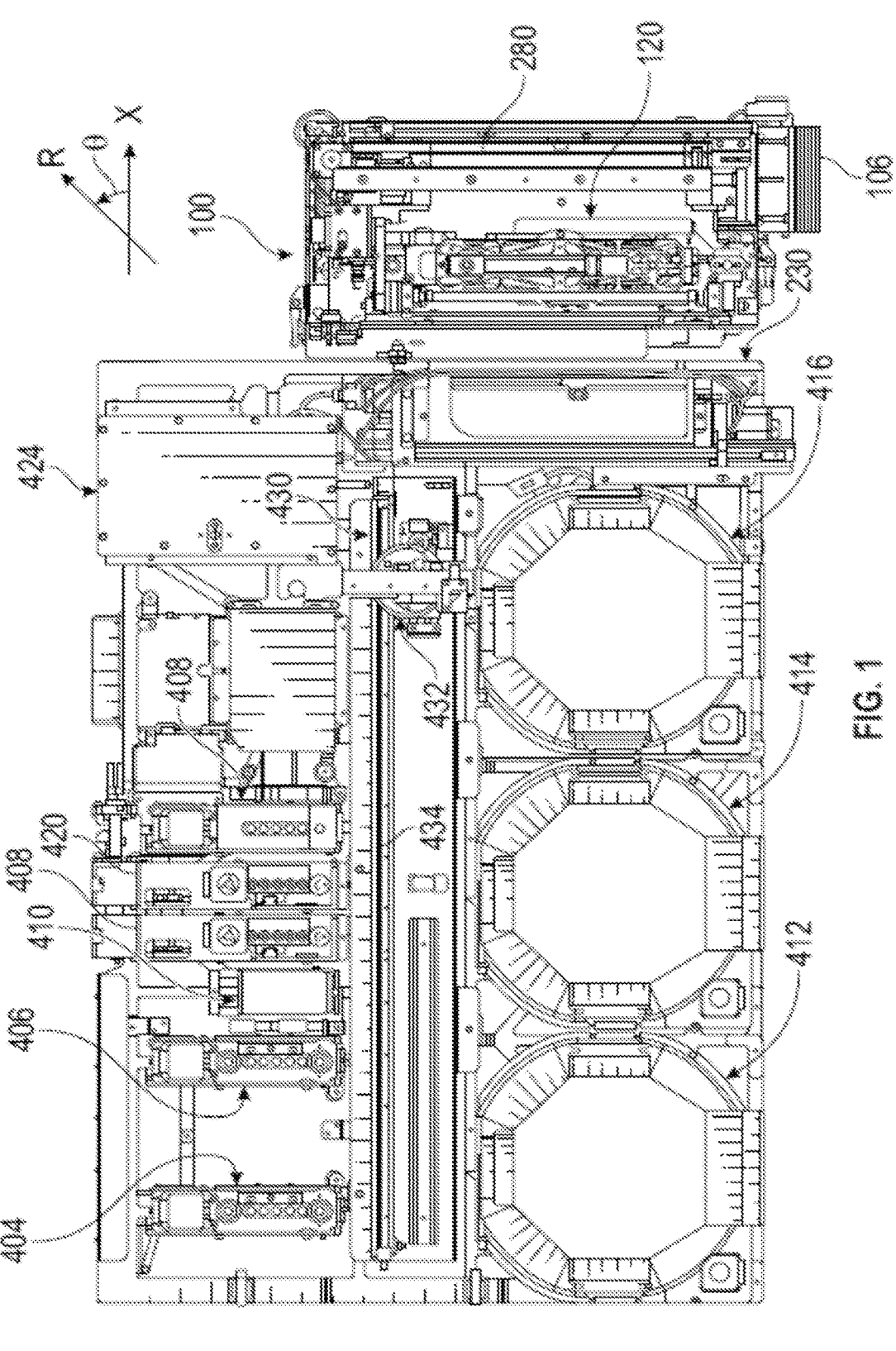
FIG. 1 is a schematic view of an analyzer.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

The use of the term "about" applies to all numeric values specified herein, whether or not explicitly indicated. This term generally refers to a range of numbers that one of ordinary skill in the art would consider as a reasonable amount of deviation to the recited numeric values (i.e., having the equivalent function or result) in the context of the present disclosure. For example, and not intended to be limiting, this term can be construed as including a deviation of ±10 percent of the given numeric value provided such a deviation does not alter the end function or result of the value. Therefore, under some circumstances as would be appreciated by one of ordinary skill in the art a value of about 1% can be construed to be a range from 0.9% to 1.1%.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

As used herein, the terms "optional" and "optionally" mean that the subsequently described, component, structure, element, event, circumstance, characteristic, property, step, etc. may or may not be included or occur and that the description includes instances where the component, structure, element, event, circumstance, characteristic, property, step, etc. is included or occurs and instances in which it is not or does not.

Definitions

Reactions or processes: According to various embodiments, reactions or processes can comprise one or more of a sample preparation process, a washing process, a sample purification process, a pre-amplification process, a pre-amplified product purification process, an amplification process, an amplified product purification process, a separation process, a sequencing process, a sequencing product purification process, a labeling process, a detecting process, or the like.

Processing components: Processing components can comprise components performing reactions or processes and include sample preparation components, purification components, pre-amplification reaction components, amplification reaction components, sequencing reaction components, detecting components or the like.

An "assay" as used herein is a procedure for detecting and/or quantifying an analyte in a sample. A sample comprising or suspected of comprising the analyte is contacted with one or more reagents and subjected to conditions permissive for generating a detectable signal informative of whether the analyte is present or the amount (e.g., mass or concentration) of analyte in the sample.

A "molecular assay" as used herein is a procedure for specifically detecting and/or quantifying a target molecule, such as a target nucleic acid. A sample comprising or suspected of comprising the target molecule is contacted with one or more reagents, including at least one reagent specific for the target molecule, and subjected to conditions permissive for generating a detectable signal informative of whether the target molecule is present. For example, where the molecular assay is PCR, the reagents include primers specific for the target and the generation of a detectable signal can be accomplished at least in part by providing a labeled probe that hybridizes to the amplicon produced by the primers in the presence of the target. Alternatively, the reagents can include an intercalating dye for detecting the formation of double-stranded nucleic acids.

An "in vitro diagnostic" or "IVD" is a product used to perform an assay on a biological sample in isolation from the source of the sample. IVDs can detect diseases, conditions, infections, metabolic markers, or quantify various constituents of bodily materials/fluids. Where the source is a multicellular organism, a sample is generally obtained from the organism and then subjected to analytical procedures (e.g., amplification and/or binding reactions) in are artificial environment, e.g., a reaction vessel. An IVD is a regulated product, such as one requiring CE marking or approval by a governmental agency, such as the Food and Drug Administration.

A "lab developed test" or "LDT" is an assay designed, validated and used by a laboratory, where kits or devices for performing the assay are not commercially marketed or sold as a product for use by other laboratories.

A "reagent" as used herein refers to any substance or combination thereof that participates in an assay (e.g., a molecular assay), other than sample material and products of the assay. Exemplary reagents include nucleotides, enzymes, amplification oligomers, probes, and salts.

Analyzer: Automated clinical analyzers ("analyzers") may comprise one or more processing components and include molecular analyzers, clinical chemistry analyzers, automated immunoassay analyzers, or any other type of in vitro diagnostics (IVD) testing analyzers. Generally, an analyzer performs a series of automated reactions or processes, such as, IVD tests on a plurality of patient samples. Patient samples may be loaded into an analyzer (manually or via an automated system), which can then perform one or more reactions or processes, such as, immunoassays, chemistry tests, or other observable tests on each sample.

Module: A module is a component that performs specific task(s) or function(s). Examples of modules may include: a pre-analytic module, which manipulates a sample container or prepares a sample for analytic testing, (e.g., a decapper module, which removes a cap from a sample container, a centrifuge, a liquid level detection module, etc.); an analytic module, such as an analyzer, which extracts a portion of a sample from a sample container and performs tests or assays comprising one or more reactions or processes; a post-analytic module, which prepares a sample container for storage after analytic testing (e.g., a capper, or recapper, module, which reseals a sample container); or a sample container handling module, such as an input module, an output module, or a storage module.

Computer or processor: A computer or processor may refer to one or more computers or processors and/or related software and processing circuits. This may include single or multicore processors, single or multiple processors, embedded systems, or distributed processing architectures, as appropriate, for implementing the specified function or functions in each embodiment.

Analyzer Overview

An exemplary analyzer 400 with which the system and method described herein may be used is shown in FIG. 1. The analyzer 400 may comprise an instrument for performing a biological, chemical, biochemical, or other multi-step analytical process. As shown in FIG. 1, the analyzer 400 may be combined with one or both of a transporter/storage module 100 for transporting and holding a supply of consumables to be provided to the analyzer 400 and an input module 230 configured to receive consumables from the transporter/storage module 100 and to present the consumables for input into the analyze 400 by a distributor mechanism within analyzer 400. Further details of an exemplary analyzer 400 are described below.

Transporter/storage module 100 includes a housing and one or more vertically-spaced holding shelves vertically stacked beneath the loading drawer 280 (not visible in FIG. 1). An access door 106 may be opened to permit a loading drawer 280 to be withdrawn from housing so that a plurality of consumables may be placed thereon and then provided to transporter/storage module 100 by inserting loading drawer 280 into the housing. The consumables may be supported on carriers configured to be supported on loading drawer 280 or on one of the holding shelves within the housing.

A transporter 120 is configured to remove the consumables from loading drawer 280 or one of the holding shelves, for example, by removing a carrier on which the consumables are supported from the loading drawer 280 or holding shelf. Transporter 120 is further configured to move a group of consumables, e.g. a carrier supporting the consumables, or an empty carrier to loading drawer 280 or to one of the holding shelves 104. A vertical transport mechanism is coupled to the transporter 120 and is configured to move the transporter 120 in a vertical direction (up or down) between the loading drawer 280 and holding shelves. In one example, the vertical transport mechanism comprises a transport elevator 210 that moves transporter 120, and the consumables (and carrier) supported thereon, vertically within the housing 102.

Input module 230 is configured to receive consumables (for example consumables supported on a carrier) transported by transporter 120 from one of the holding shelves into the input module 230. In an embodiment, the input module 230 may be incorporated into a housing of the analyzer 400. From the input module 230, the consumables are selectively retrieved into the analyzer 400 and are moved about or otherwise manipulated within the analyzer. After all the consumables have been removed from the carrier within the input module 230, the transporter 120 will move the empty carrier from the input module 230 to the loading drawer 280 or one of the holding shelves. Further details of the input module 230 and the transporter/storage module 100 are described in U.S. Provisional Patent Application No. 62/815,184, filed Mar. 7, 2019, entitled "System and Method for Transporting and Holding Consumables in a Processing Instrument."

As shown in FIG. 1, processing instrument 400 may include various modules configured to receive one or more receptacles (examples of which are described in more detail below) within each of which may be performed one or more steps of a biological, chemical, biochemical, or other multistep analytical process. The modules of the analyzer 400 constitute receptacle-receiving structures configured to receive and hold one or more receptacles.

Analyzer 400 may further include load stations 404, 406, 408 configured to receive receptacles and within which one or more materials, including assay reagents, may be added to the receptacles, e.g., by an automated pipettor (not shown), including sample material and various reaction reagents.

Analyzer 400 may further comprise one or more parking stations 410 for holding receptacles containing reaction mixtures prior to subsequent processing within another module of the analyzer 400. Parking stations 410 may include magnets for attracting magnetically-responsive solid supports to the inner walls of receptacles, thereby pulling the solid supports out of suspension. An exemplary parking station is described in U.S. Pat. No. 8,276,762.

Analyzer 400 may include one or more incubators 412, 414, 416 configured to receive a plurality of receptacles and to heat (and/or maintain) the contents of the receptacles at a temperature higher than ambient temperature. The illustrated embodiment includes three incubators 412, 414, 416, each of which may be configured to heat and/or maintain the contents of the receptacles at a different temperature. Exemplary incubators are described in U.S. Pat. Nos. 7,964,413 and 8,718,948.

Analyzer 400 may include sample-processing devices, such as magnetic wash stations 418, 420, adapted to separate or isolate a target nucleic acid or other analyte (e.g., immobilized on a magnetically-responsive solid support) from the remaining contents of the receptacle. Exemplary magnetic wash stations are described in U.S. Pat. Nos. 6,605,213 and 9,011,771.

Analyzer 400 may further include a detector 424 configured to receive a receptacle and to detect a signal (e.g., an optical signal, such as fluorescence or chemiluminescence) emitted by the contents of the receptacle. In one implementation, detector 424 may comprise a luminometer for detecting luminescent signals emitted by the contents of a receptacle and/or a fluorometer for detecting fluorescent emissions from the contents of the receptacle. Analyzer 400 may also include one or more signal detecting devices, such as, for example, fluorometers (e.g., coupled to one or more of incubators 412, 414, 416) configured to detect (e.g., at periodic intervals) signals emitted by the contents of receptacles contained in the incubators while a process, such as nucleic acid amplification, is occurring within the reaction receptacles. Exemplary luminometers and fluorometers are described in U.S. Pat. Nos. 7,396,509 and 8,008,066.

The analyzer 400 further includes a receptacle transport apparatus, which, in the illustrated embodiment, comprises a receptacle distributor 430. Each of the modules of the analyzer 400 includes a receptacle transfer portal through which receptacles are inserted into or removed from the respective module. Each module may or may not include an openable door covering its receptacle portal. Receptacle distributor 430 is configured to move receptacles between the various modules and retrieve receptacles from the modules and deposit receptacles into the modules. More specifically, receptacle distributor 430 includes a receptacle distribution head 432 configured to move in an X direction along a transport track 434, rotate in a theta (Θ) direction, and move receptacles in an R direction into and out of the receptacle distribution head 432 and one of the modules of analyzer 400. The receptacle distributor 430 may further be configured to remove receptacles, one-at-a-time, from the input module 230 described herein.

In operation, receptacle distribution head 432 moves in the X direction along the transport track 434 to a transfer position with respect to one of the modules or the input module 230. The distribution head then rotates in the Θ direction to place the distribution head in a receptacle transfer orientation with respect to the receptacle transfer portal of the module or the input module 230. A receptacle moving mechanism, e.g. a linearly-actuated hook, moves in an R direction with respect to the distribution head 432 to move a receptacle from the distribution head 432 into the module or to retrieve a receptacle from the module or input module 230 into the distribution head 432. In an embodiment, receptacle distributor 430 further includes means for effecting vertical (Z-axis, normal to the page of FIG. 1) position adjustment of the distribution head 432 to accommodate variations in vertical position of the receptacle transfer portals of the various modules. Receptacle distributor 430 may include structural elements and associated control logic for opening a door that is covering a receptacle transfer portal before inserting a receptacle into the module or removing the receptacle from the module.

An exemplary receptacle transport apparatus, exemplary receptacle transfer portal doors, and mechanisms for opening the doors are described in U.S. Pat. No. 8,731,712.

Exemplary analyzers include analyzers described in U.S. Pat. Nos. 8,731,712 and 9,732,374 and International Patent Application No. PCT/US2018/041472, as well as the Panther® and Panther Fusion® systems available from Hologic, Inc. (Marlborough, MA). Systems, methods, and computer readable medium for enabling a user to specify user-defined assay parameters of an assay protocol to be performed on an automated analyzer, such as in vitro diagnostic ("IVD") assays and lab developed assays (referred to herein as "Lab Developed Tests" or "LDTs") that are developed, validated and used by a customer or other third party are described in International Patent Application Publication No. WO 2019/148169 (PCT/US2019/015589), entitled "Analytical Systems and Methods."

Figure 2:
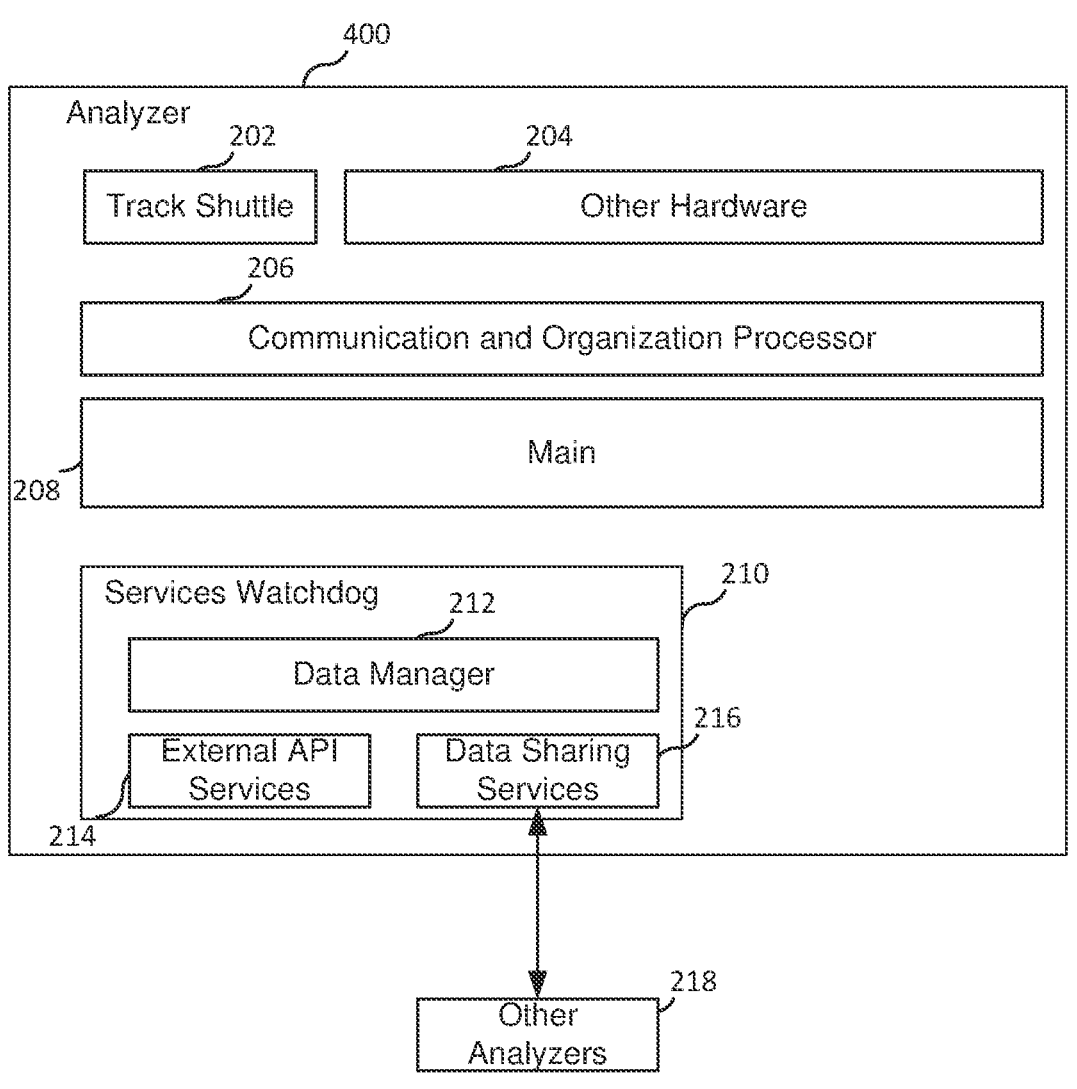
FIG. 2 is a schematic view of an analyzer.

FIG. 2 illustrates a component view of the analyzer 400. As shown, analyzer 400 may have a number of different software and hardware related modules. For example, analyzer 400 may include a track shuttle 202 for transferring sample containers and/or other items between the analyzer 400 and an automated conveyance track, for example, as described in U.S. Provisional Patent Application Ser. No. 62/842,585, and other hardware 204, such as the transporter/ storage module 100. There may be a Communication and Organization Processor (COP) layer 206 operating between the software and hardware components. Main module 208 may be responsible for much of the software-related tasks of analyzer 400, including for instance communicating with external components such as a blood bank (BB) or a laboratory information system (LIS) (not shown). Analyzer 400 may also include a services watchdog 210, which may house a data manager 212, an external API services 214, and a data sharing services 216. In some embodiments, data sharing services 216 may contain some or all of the logic for implementing the data sharing approaches described herein. Although data sharing services 216 is shown as being part of analyzer 400 in FIG. 2, in some embodiments, data sharing services 216 may be an external node communicatively coupled to analyzer 400. Data sharing services 216 may communicate with other analyzers 400, e.g. using an encrypted communication link.

System Overview

Two or more analyzers may be configured to operate together (e.g., in a laboratory setting) so that data may be effectively shared between them. The data sharing among the analyzers may include sharing of information about assay reagents, including information such as an amount of the assay reagent remaining and an expiration date of the assay reagent. Such information can facilitate the sharing of reagents among different analyzers, such that a given reagent may be used in a first analyzer for a first time period, and then switched to a second analyzer for a second, non-overlapping time period. Because information about the assay reagent is shared, the second analyzer in this example will be able to receive the assay reagent for performing a molecular assay and correlate the information with the received assay reagent. The second analyzer will also be able to analyze the information to determine whether the assay reagent is viable, prior to performing a molecular assay with the assay reagent. If the assay reagent is viable, then the second analyzer may perform the molecular assay with the assay reagent.

DESCRIPTION OF ILLUSTRATED EMBODIMENTS

Figure 3:
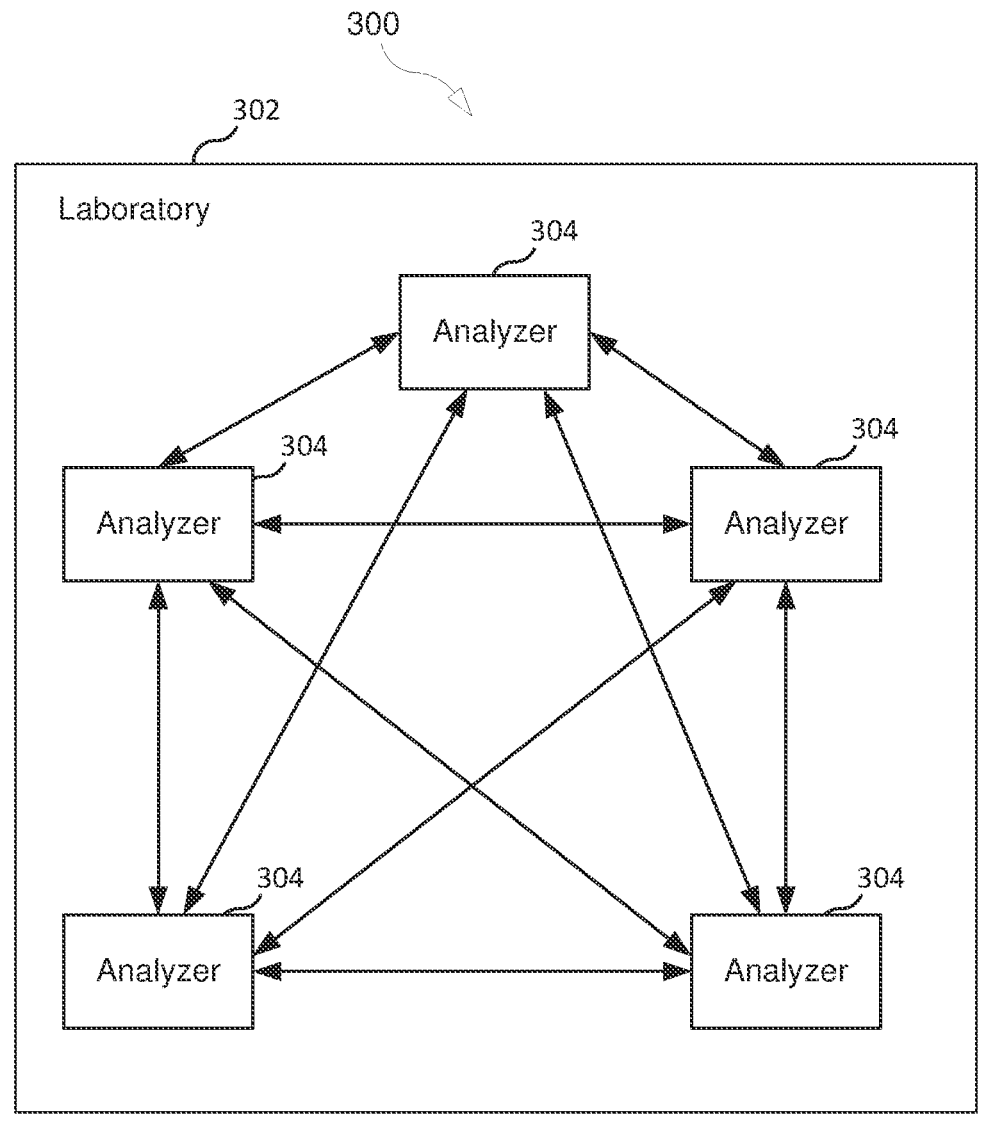
FIG. 3 is a schematic view of data sharing system according to an embodiment.

FIG. 3 illustrates system 300, according to an embodiment. System 300 includes five analyzers 304 in a laboratory environment 302. In embodiments, system 300 may include fewer analyzers 304 or more analyzers 304, such as two analyzers 304, ten analyzers 304, or twenty analyzers 304, and generally may include any number of analyzers 304 greater than or equal to two. In some embodiments, the number of analyzers 304 permitted in system 300 to share data with each other may be limited (e.g., to 16 analyzers 304 in a data sharing group). As shown, each analyzer 304 may be communicatively coupled to each other analyzer 304 with a bidirectional link. For example, each analyzer 304 may be able to communicate wirelessly (such as over WiFi or a cellular signal) with each other analyzer 304, or may be able to communicate via a wired connection (such as over a fiber-optic cable). In other embodiments, analyzers 304 may be communicatively coupled in different network topologies, e.g. in a star topology, or a ring topology, such that a given analyzer 304 may not be able to communicate directly with another analyzer 304, but may have to go through one or more intermediary analyzers 304 to reach the another analyzer 304. In some embodiments, communication from one analyzer 304 to another analyzer 304 (whether direct or indirect) may be performed securely, such as through using encryption.

Analyzer 304 may be any analyzer suitable for performing assays (e.g., molecular assays). For example, analyzer 304 may be the analyzer 400 discussed with respect to FIGS. 1-2. In some embodiments, input into the analyzers 304 (such as reagents and samples) may be provided manually by laboratory technicians. The system 300 may, in some embodiments, also include a "track system," such as a shuttle module (an electromechanical system) that allows for an external robot to transfer items (such as reagents or samples) to and from the different analyzers 304 in the system 300. In such embodiments, input into the analyzers 304 may be provided automatically by the track system, such as by scanning machine-readable labels (e.g., bar codes or RFID tags) associated with each sample and reagent container to access unique identification information and then correlating the unique identification information with attributes of the sample or reagent, as applicable, stored in a database, such as a laboratory information system.

Data sharing may be implemented as a subsystem in each of the analyzers 304 in system 300. Data sharing allows analyzers 304 to electronically share information with each other. Any type of electronic (digital) information may be shared. In particular, examples of information (data) that may be shared among analyzers 304 include information about users; master lots for assay reagents, controls, and/or calibrators; assay reagent kits; assay cartridges; and external quality control (EQC) definitions.

Users refer to laboratory technicians that are authorized to use one or more of the networked analyzers 304. A user may be required to perform an authorization procedure (e.g., login with username and password) prior to accessing a particular analyzer 304. Before a user can do that, the user may also need to be registered with the analyzer; for example, a user account may need to be created giving that user certain permissions, such as specifying which analyzers 304 the user may access. By sharing user information among analyzers 304, a user can register on a single analyzer 304 and have that information automatically shared with each other networked analyzer 304 in the same laboratory environment 302.

Master lots for assay reagents, controls, and/or calibrators refer to additional components which may have information to be shared between analyzers 304. A master lot refers to a set of manufactured kit components, e.g., reagents and consumables, that must be used together to perform an assay. A master lot sheet refers to a sheet of information (e.g., a barcode sheet) that contains useful information about the master lot, such as calibration coefficients and batch number information for reagents. A reagent master lot sheet contains the reagent lots that belong to the master lot and all reagent coefficients (e.g., ratio values for calibrators). A calibrator master lot sheet contains calibrator concentrations. A control master lot sheet contains control concentrations. By sharing master lot information among analyzers 304, different analyzers 304 may have access to important information about the master lots, even if a particular analyzer 304 has not seen the particular master lot before.

Assay reagent kits refer to a kit that may include one or more kinds of reagent of a certain quantity (for example, stored in one or more test tubes). A reagent kit may also include additional items other than the reagent. Reagent kits may have information associated with them, such as a "kind," a "status," and an "expiration date." By sharing assay reagent kit information among analyzers 304, different analyzers 304 may have access to important information about the assay reagent kit, even if a particular analyzer 304 has not seen the particular assay reagent kit before.

Assay cartridges refer to devices which may contain reagents. Cartridges may be used as part of performing an assay. For example, the reagents contained in an assay cartridge may have a specific expiration date associated with it. By sharing assay cartridge information among analyzers 304, different analyzers 304 may have access to important information about the assay cartridge, even if a particular analyzer 304 has not seen the particular assay cartridge before.

EQC definitions refer to a site-specific control that may be used for a given assay. For example, a given laboratory environment 302 may define an EQC related to an assay that it runs. By sharing such EQC information, a user can enter an EQC definition at one analyzer 304 and have that definition automatically be reflected at other analyzers 304 in the same laboratory environment 302.

Figure 4:
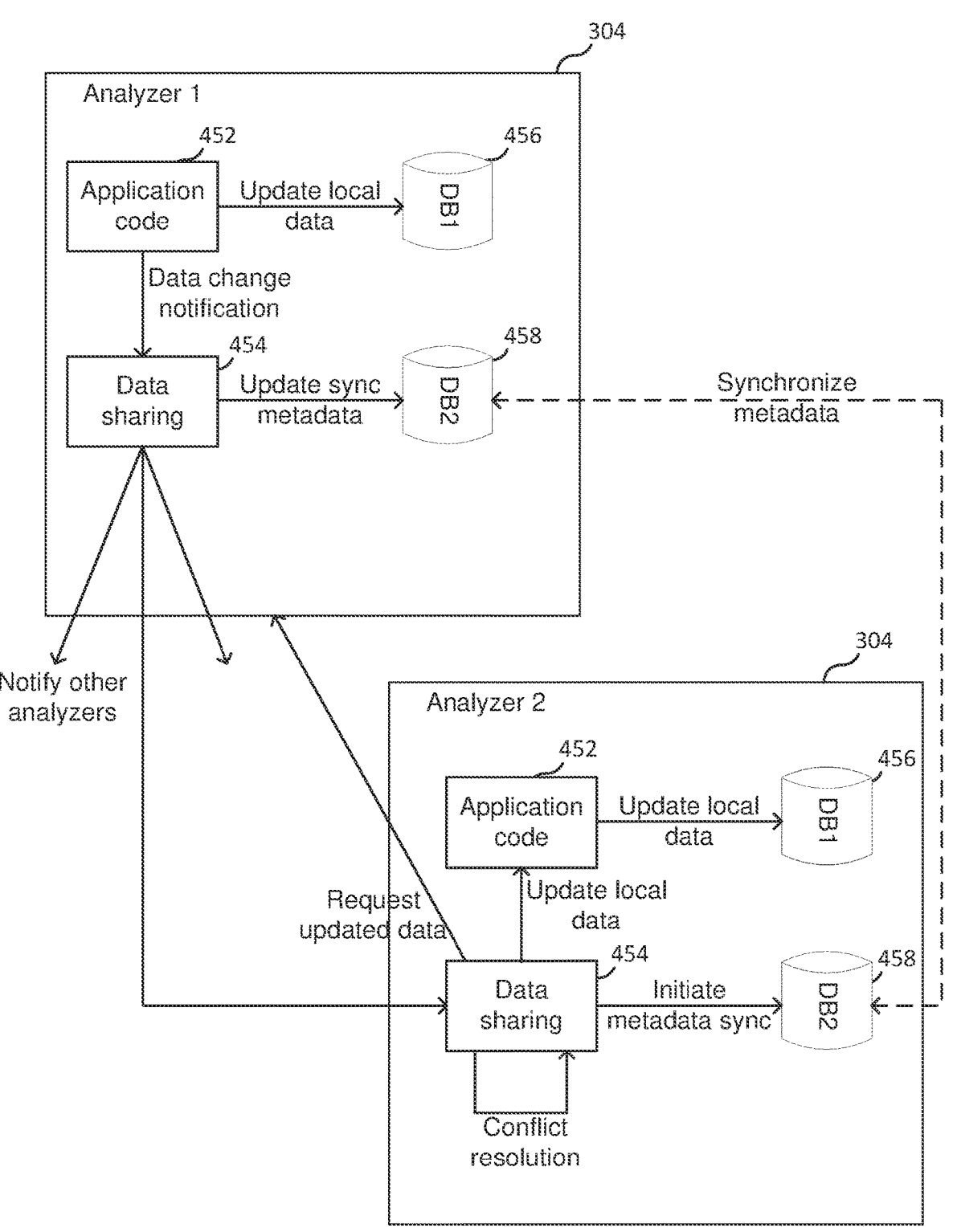
FIG. 4 is a schematic view of data sharing system according to an embodiment.
Figure 5:
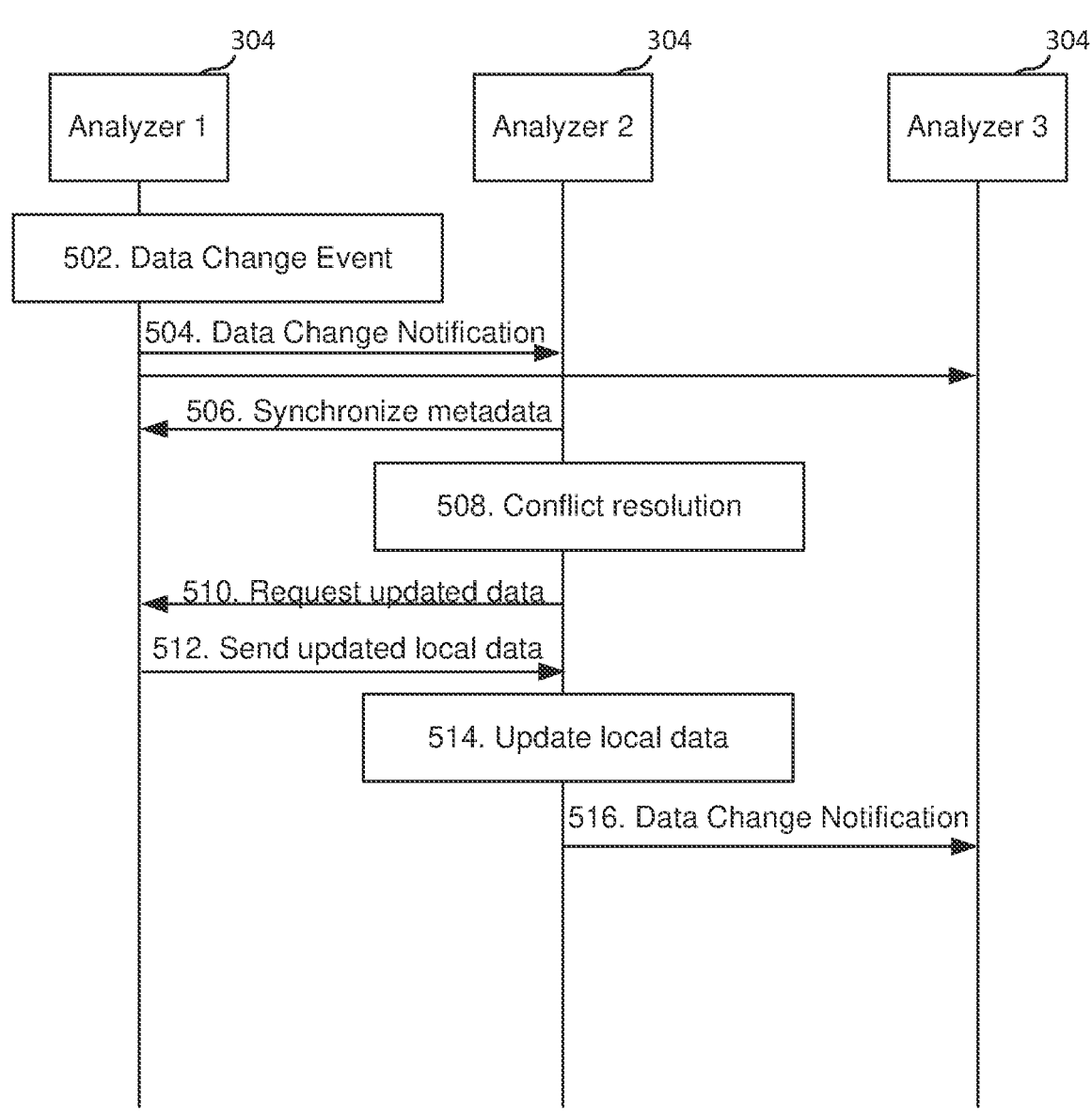
FIG. 5 is a message flow diagram according to an embodiment.

FIGS. 4-5 illustrates data sharing among analyzers 304 according to an embodiment. Data (such as data about users; master lots for assay reagents, controls, and/or calibrators; assay reagent kits; assay cartridges; and EQC definitions; or such as described in appendices enclosed herein) is shared among analyzers 304 in some embodiments by pushing out changes as they occur. For example, if a data change event happens (for example, upon loading a reagent kit) at a first analyzer 304 ("Analyzer 1") (at 502), then application code 452 on the first analyzer may detect the data change event. Upon detection, application code 452 may then update its local data 456 ("DB1") and notify data sharing unit 454. Data sharing unit 454 may then update its synchronized metadata. 458 and notify other analyzers (at 504), including a second analyzer 304 ("Analyzer 2").

Upon the second analyzer 304 receiving a notification of change (at 504), the second analyzer 304 processes the notification of change. In some embodiments, the notification of change received from the first analyzer includes metadata regarding the nature of the change that occurred. In some embodiments, the second analyzer 304 may need to initiate a metadata synchronization (at 506) with the first analyzer 304 in order to receive additional information regarding the nature of the change. In either event, the second analyzer 304 next determines (at 508) whether the second analyzer 304 needs the updated information from the first analyzer. This process (referred to a conflict resolution) is described in more detail elsewhere in this disclosure.

In some instances, the second analyzer 304 may determine that it has already received the updated information; for example, the second analyzer 304 may have received an earlier notification of change from a third analyzer 304 that included the same updated information, and therefore there is no need for the second analyzer 304 to proceed further in processing the notification of change. If the second analyzer 304 determines that it needs the updated information, it will request the updated data (at 510) from the first analyzer 304. Upon receiving the request, the first analyzer 304 will then send this information back to the second analyzer 304 (at 512). Data sharing unit 454 on the second analyzer 304 may pass the updated local data to application code 452, which then updates local data 456 with the updated information (at 514).

In some embodiments, an analyzer 304 may seek to synchronize with one or more other analyzers 304 even when it does not receive a change notification. For example, when an analyzer 304 first comes online, it may synchronize with other analyzers 304, since the analyzer 304 would not have received any change notifications while it was offline. This may occur as a result of the analyzer 304 being turned on, the analyzer 304 resetting from a crash or system failure or network failure, or for other reasons.

In some embodiments, analyzers 304 maintain both a local data 456 and a synchronized metadata 458. The synchronized metadata 408 describes the nature of the change, including information such as the last modified time, so that analyzers 304 can determine whether they need the change. If so, then those analyzers 304 may request the underlying change data from the appropriate analyzer 304. In some embodiments, analyzers 304 may store their data (e.g., in local data 406) in a particular schema, and if different analyzers 304 are running different versions of software, then there may be multiple schemas among the different analyzers 304. The synchronized metadata may be designed to be forward and backward compliant, such that any version of analyzer 304 may be able to determine whether needs updated data based on the metadata. Then, when a first analyzer 304 requests updated data from a second analyzer 304, the first analyzer 304 may receive data in the appropriate schema in the following manner: if the first analyzer 304 is a more recent version than the second analyzer 304, the first analyzer 304 contains software to convert the schema provided by the second analyzer 304, and if the second analyzer 304 is a more recent version than the first analyzer 304, the second analyzer 304 contains software to convert the schema before it is provided to the first analyzer 304.

As the number of analyzers 304 increases, the communication costs also increase. For a small number of analyzers 304 (e.g., less than 16), where the data exchanged between analyzers is relatively small (e.g., on the order of 100 KB or less), and where the number of data change events per a given time instance is also relatively small (e.g., less than 1,000 data sharing operations per hour per analyzer), then a peer-to-peer architecture where every analyzer 304 communicates with every other analyzer 304 may make the most sense. However, as communication costs increase, alternative embodiments may be necessary. For example, in some embodiments different network topologies could be enforced, controlling which analyzers 304 communicate with which other analyzers 304. As an example, a first set of analyzers 304 may each communicate with each other, and a second set of analyzers 304 may also each communicate with each other, but any communication between the first and second sets could be mediated by one or two analyzers 304. Depending on usage and particular laboratory environment 302, other network topologies may also improve communication cost. In some embodiments, a master node may control communication throughout system 300. The master node may be part of an individual analyzer 304 or may be a separate node in system 300. In some embodiments, the master node may require all communication to go through the master node.

Conflict resolution in system 300 generally uses the rule that the last edit wins. That is, the latest change is the correct one. For example, if the incoming data is the same as the local data, then there is no conflict and no additional processing is necessary. As indicated elsewhere, this may be the case where one analyzer 304 has already received the updated information from another analyzer 304, but the updated information is being propagated by additional analyzers 304. In another case, a primary key of the incoming data may not be present on the analyzer 304, indicating that the analyzer 304 does not have an old version of the incoming data. There also is no conflict in this case, and the analyzer 304 can simply accept the incoming data. A conflict occurs when the analyzer 304 has an old version of the incoming data. If the last modified time of the local data on analyzer 304 is earlier than the last modified time of the incoming data, then generally the incoming data should be accepted as the most recent. If, on the other hand, the last modified time of the local data is later than the last modified time of the incoming data, then generally the incoming data should be discarded as outdated.

Exceptions to the general conflict resolution process may apply for specific types of data. For example, for updates regarding a user, regardless of last modified time, if one of the instances is marked as "deleted" then the "deleted" instance should win the conflict. This may also apply to other types of data where a "deleted" field may be used, such as for ECQ definitions or LDT calibrations. Similarly, if a reagent kit has a status marked as "invalid," then regardless of time, the instance with the "invalid" status should win the conflict. For master lots, the later expiration date should win the conflict (this ensures that a master lot that has been date extended will be shared to the group).

In order to determine a last modified time accurately, in some embodiments each analyzer 304 may determine time offsets for each other analyzer 304. This may be necessary in some embodiments, because generally the internal clock of the analyzers 304 are not synchronized and it may be difficult to synchronize the clocks generally because once an assay is begun, it could affect the results of the assay to modify the internal clock. In some embodiments, analyzers 304 may also keep a special clock for synchronizing data, and may synchronize this clock among the different analyzers 304.

Computing Time Offsets

To manage clock differences among analyzers, in some embodiments time offsets may be regularly calculated and stored in each analyzer, e.g. at periodic intervals or based on certain events, such as when data change events are processed.

Time offset calculations may also be shared with other analyzers so that other analyzers are working with the same time offset values when doing conflict resolution. If an analyzer is not available when an offset calculation is done, the offset for that analyzer may be recorded as a the last known or computed value for that analyzer.

Each analyzer maintains a clock offset for all other analyzers relative to itself. When a data change is received, the change has a time stamp indicating when the change was made. In order to compare that time to the last time the local data was changed, the time values need to be normalized. This is done by adding the appropriate offset to the time stamp of the change, where "appropriate" means the offset for the instrument that supplied the data change.

One algorithm for determining time offsets may proceed as follows: A packet will be sent from analyzer A to analyzer B. The time it is sent is stored as $A_{Sent}$. Analyzer B will respond with analyzer B's current time which is stored as $B_{Sent}$. Analyzer A will receive the packet and store that time as $A_{Received}$. Analyzer A calculates the difference between $A_{Sent}$ and $B_{Sent}$ to find the difference in clock time. Analyzer A calculates the average travel time of the sent and received packets by dividing the difference between $A_{Sent}$ and $A_{Received}$ by 2. The offset is then calculated as the difference in clock time minus the estimated travel time.

This algorithm assumes that the travel time will be similar from A→B then back from B→A. This is essentially equivalent to:

$$\frac{(\mathit{Diff}(A, B) - Tx) + (\mathit{Diff}(A, B) + Tx)}{2}$$

where Tx is the transfer time. The transfer times cancel out (assuming they are the same), and the result is just the difference. In embodiments, this may be repeated a number of times (e.g., 10 times), and any outliers may be removed. The remaining results may be averaged.

Figure 6:
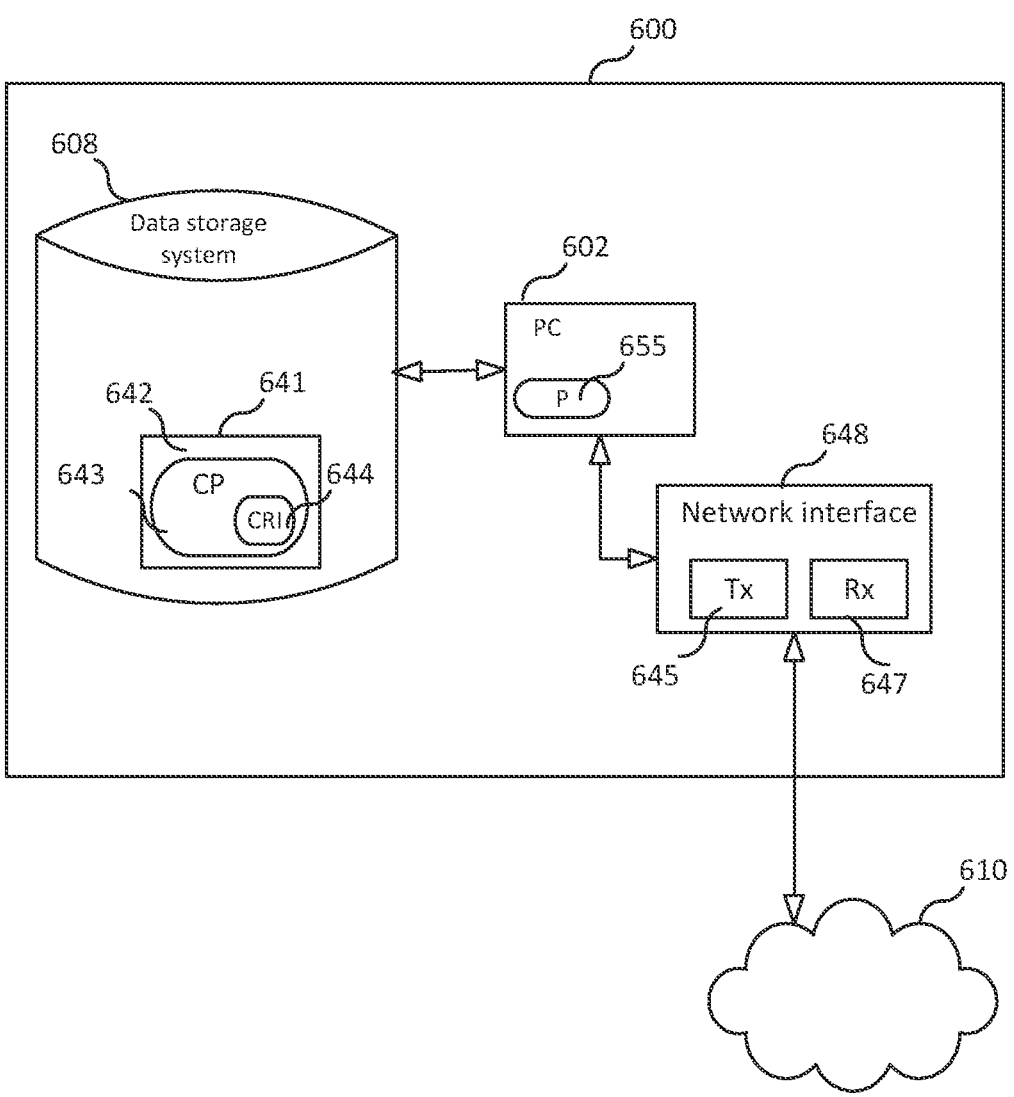
FIG. 6 is a block diagram of an apparatus according to an embodiment.

FIG. 6 is a block diagram of an apparatus 600 (e.g., an analyzer 304 or master node), according to some embodiments. As shown in FIG. 6, the apparatus may comprise: processing circuitry (PC) 602, which may include one or more processors (P) 655 (e.g., a general purpose microprocessor and/or one or more other processors, such as an application specific integrated circuit (ASIC), field-programmable gate arrays (FPGAs), and the like); a network interface 648 comprising a transmitter (Tx) 645 and a receiver (Rx) 647 for enabling the apparatus to transmit data to and receive data from other nodes connected to a network 610 (e.g., an Internet Protocol (IP) network) to which network interface 648 is connected; and a local storage unit (a.k.a., "data storage system") 608, which may include one or more non-volatile storage devices and/or one or more volatile storage devices. In embodiments where PC 602 includes a programmable processor, a computer program product (CPP) 641 may be provided. CPP 641 includes a computer readable medium (CRM) 642 storing a computer program (CP) 643 comprising computer readable instructions (CRI) 644. CRM 642 may be a non-transitory computer readable medium, such as, magnetic media (e.g., a hard disk), optical media, memory devices (e.g., random access memory, flash memory), and the like. In some embodiments, the CRI 644 of computer program 643 is configured such that when executed by PC 602, the CRI causes the apparatus to perform steps described herein (e.g., steps described herein with reference to the flow charts). In other embodiments, the apparatus may be configured to perform steps described herein without the need for code. That is, for example, PC 602 may consist merely of one or more ASICs. Hence, the features of the embodiments described herein may be implemented in hardware and/or software.

Figure 7:
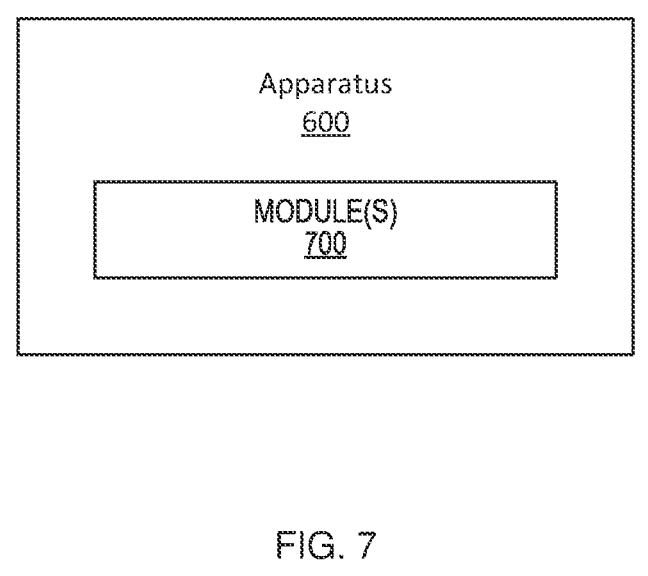

FIG. 7 is a schematic block diagram of the apparatus 600 according to some other embodiments. The apparatus 600 includes one or more modules 700, each of which is implemented in software. The module(s) 700 provide the functionality of apparatus 600 described herein (e.g., the steps herein, e.g., with respect to FIGS. 4-5).

While the subject matter of this disclosure has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

The invention claimed is:

1. A method for sharing system information data in a network of two or more diagnostic instruments for performing assays, wherein the system information data comprises operating information for the diagnostic instruments in the network, the method comprising:

receiving a system information metadata packet by a first diagnostic instrument in the network, wherein the system information metadata packet is associated with system information data on a second diagnostic instrument in the network and comprises one or more attributes of a system information data packet containing the associated system information data;

determining from the system information metadata packet that the first diagnostic instrument needs the associated system information data contained in the system information data packet by comparing the one or more attributes of the system information metadata packet with local data;

in response to determining from the system information metadata packet that the first diagnostic instrument needs the associated system information data contained in the system information data packet, sending a request to the second diagnostic instrument to send the system information data packet;

receiving the system information data packet containing the associated system information data from the second diagnostic instrument;

in response to receiving the system information data packet containing the associated system information data from the second diagnostic instrument, updating the local data based on the associated system information data from the second diagnostic instrument; and operating the first diagnostic instrument to perform an assay using the updated local data.

2. The method of claim 1, wherein the system information data further comprises information about at least one of the following: users, master lots for assay reagents, controls, calibrators, assay reagent kits, assay cartridges, and external quality control (EQC) definitions.

3. The method of claim 1, wherein comparing the one or more attributes of the system information metadata packet with local data comprises comparing a first time with a second time, wherein the first time represents when the system information data was last changed and the second time represents when the local data was last changed.

4. The method of claim 3, wherein comparing a first time with a second time comprises normalizing the first time by adding an offset corresponding to the second diagnostic instrument, wherein the offset is calculated based on a difference in clock time for the second diagnostic instrument and an estimated travel time from the second diagnostic instrument to the first diagnostic instrument.

5. The method of claim 4, wherein multiple values for the difference in clock time and the estimated travel time are determined from repeating the calculation and the offset is calculated based on an average of the multiple values for the difference in clock time and the estimated travel time.

6. A network of analyzers for performing assays, each analyzer in the network of analyzers comprising a processor and instructions stored on a non-transient computer readable medium which, when executed, cause the processor to:

receive a system information metadata packet by a first analyzer in the network of analyzers, wherein the system information metadata packet is associated with system information data on a second analyzer in the network of analyzers and comprises one or more attributes of a system information data packet containing the associated system information data;

determine from the system information metadata packet that the first analyzer needs the associated system information data contained in the system information data packet by comparing the one or more attributes of the system information metadata packet with local data;

in response to determining from the system information metadata packet that the first analyzer needs the associated system information data contained in the system information data packet, send a request to the second analyzer to send the system information data packet;

receive the system information data packet containing the associated system information data from the second analyzer;

in response to receiving the system information data packet containing the associated system information data from the second analyzer, update the local data based on the associated system information data from the second analyzer; and operate the first analyzer to perform an assay using the updated local data.

7. The network of claim 6, wherein the system information data comprises information about at least one of the following: users, master lots for assay reagents, controls, calibrators, assay reagent kits, assay cartridges, and external quality control (EQC) definitions.

\* \* \* \* \*